(12) United States Patent
Brackett et al.

(10) Patent No.: US 6,982,639 B2
(45) Date of Patent: Jan. 3, 2006

(54) WIRELESS SUBJECT LOCATOR

(75) Inventors: C. Cameron Brackett, Naperville, IL (US); Steven L. Fors, Chicago, IL (US); Mark M. Morita, Arlington Heights, IL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 42 days.

(21) Appl. No.: 10/304,568

(22) Filed: Nov. 26, 2002

(65) Prior Publication Data

US 2004/0100377 A1    May 27, 2004

(51) Int. Cl.
*H04Q 7/00*   (2006.01)
(52) U.S. Cl. .......................... 340/539.13; 340/286.07; 340/539.11; 340/539.12; 340/573.1
(58) Field of Classification Search ........... 340/539.11, 340/539.12, 539.13, 573.1, 573.4, 286.07
See application file for complete search history.

(56) References Cited

U.S. PATENT DOCUMENTS

| 3,439,320 | A | * | 4/1969 | Ward ........................... 367/191 |
| 4,225,953 | A | * | 9/1980 | Simon et al. ................ 367/117 |
| 4,275,385 | A | * | 6/1981 | White ................... 340/825.49 |
| 4,510,495 | A |   | 4/1985 | Sigrimis et al. ....... 340/825.54 |
| 4,598,275 | A | * | 7/1986 | Ross et al. ................ 340/573.4 |
| 4,618,861 | A |   | 10/1986 | Gettens et al. .............. 128/903 |
| 5,150,310 | A |   | 9/1992 | Greenspun et al. ......... 342/451 |
| 5,218,344 | A | * | 6/1993 | Ricketts .................... 340/573.4 |
| 5,353,011 | A |   | 10/1994 | Wheeler et al. ............ 340/556 |
| 5,381,137 | A |   | 1/1995 | Ghaem et al. ................ 29/846 |
| 5,458,123 | A | * | 10/1995 | Unger ........................ 600/509 |
| 5,552,772 | A |   | 9/1996 | Janky et al. ................ 342/463 |
| 5,568,119 | A |   | 10/1996 | Schipper et al. ........ 340/825.37 |
| 5,732,401 | A | * | 3/1998 | Conway ....................... 705/29 |
| 5,842,118 | A |   | 11/1998 | Wood, Jr. .................... 455/101 |
| 5,920,261 | A |   | 7/1999 | Hughes et al. .............. 342/126 |
| 5,977,913 | A |   | 11/1999 | Christ ........................ 342/465 |
| 6,013,949 | A |   | 1/2000 | Tuttle ......................... 257/723 |
| 6,023,610 | A |   | 2/2000 | Wood, Jr. .................... 455/101 |
| 6,031,459 | A |   | 2/2000 | Lake ........................ 340/572.8 |
| 6,150,921 | A |   | 11/2000 | Werb et al. ................. 340/10.1 |
| 6,302,844 | B1 | * | 10/2001 | Walker et al. .............. 600/300 |
| 6,326,889 | B1 |   | 12/2001 | Van Horn et al. ........ 340/572.1 |
| 6,356,230 | B1 |   | 3/2002 | Greef et al. ................ 342/127 |
| 6,380,845 | B2 |   | 4/2002 | Tuttle ........................ 340/10.4 |
| 6,462,656 | B2 | * | 10/2002 | Ulrich et al. ............. 340/539.1 |
| 6,512,456 | B1 | * | 1/2003 | Taylor, Jr. ................. 340/573.1 |
| 6,616,606 | B1 | * | 9/2003 | Petersen et al. ............. 600/300 |
| 2002/0165733 | A1 | * | 11/2002 | Pulkkinen et al. ............. 705/2 |

\* cited by examiner

*Primary Examiner*—Brent A. Swarthout
(74) *Attorney, Agent, or Firm*—Andrus, Sceales, Starke & Sawall, LLP (57) ABSTRACT

A system for tracking a subject of interest in a location is disclosed. The system is used with subjects who have an identification device having a unique signal identifier. The system comprises a wireless proximity detector capable of detecting the signal identifier; a monitoring unit that monitors the proximity detector by monitoring which signal identifier has been detected by the proximity detector, the monitoring unit generating a data signal representative of which signal identifier has been detected; and a data output unit that generates location data based upon the data signal. The information can be displayed graphically or as a list and can be sorted by various criteria. The display can provide many options to make the display more useful. Also disclosed is a method for tracking a subject of interest using a unique signal identifier. Additionally, a display to be used with the system is disclosed.

27 Claims, 6 Drawing Sheets

FIGURE 8

WIRELESS SUBJECT LOCATOR

FIELD OF THE INVENTION

The invention relates to wirelessly locating a subject of interest.

BACKGROUND OF THE INVENTION

There is currently no way of effectively tracking where a physician is located in a health care facility. Often times, other staff may need to know where a doctor is, for planning purposes such as understanding when a doctor will reach a location for planning and also for assuaging patient concerns. Also, knowing where a doctor is located may allow for contacting the doctor that would be able to give the fastest response. Such a system may also provide the ability to effectively determine which physician is most available for consultation. A system that would allow other staff to locate a doctor in a hospital would be a valuable tool for providing patient care.

Further, the quickest way to find a doctor is to either phone or page them to get a response, but a person using these ways must hope that the doctor responds in a timely fashion. A graphical user interface that can not only illustrate where the doctor is, but can also allow immediate communication via paging, instant messaging, communication over the internet such as Voice Over IP, or some other communication method would allow for improved hospital communications and ultimately would add to increased quality in patient care.

Further still, effectively contacting a doctor is difficult because the best way to contact the doctor is not always clear. The best way to contact a doctor may change during the day and may change from what had been previously scheduled. A system that can identify the best way to get in contact with a doctor is needed, especially a system that can identify the best way even though there were unexpected changes in a doctor's schedule.

Also, choosing and locating an available doctor can be a difficult task. A person needing a physician's services must go through a number of physicians' schedules before finding one, only to find out that the physician has recently become occupied or is located far away. A system that can identify doctors that are both available and close would be desirable. Also, a system that could track unplanned changes in a doctor's schedule would be desirable.

BRIEF SUMMARY OF THE INVENTION

One embodiment is directed to a system for tracking a subject of interest. The system is used with an identification device having a unique signal identifier. The system comprises a wireless proximity detector capable of detecting an identification signal. The system also comprises a monitoring unit that monitors the proximity detector; the monitoring unit monitors which signal identifiers have been detected by the proximity detector. The monitoring unit also generates a data signal representative of which signal identifiers have been detected by the proximity detector. The system further comprises a data output unit that generates location data based upon the data signal.

Another embodiment provides a method for tracking a subject of interest. The method comprises assigning a unique signal identifier to the subject. The method also comprises detecting the signal identifier using a wireless proximity detector and monitoring the proximity detector for detection of the unique signal identifier. Further, the method comprises displaying output data representative of the location of the subject of interest, based on the results of the monitoring.

Another embodiment is directed to a display for indicating a location of a health care worker to a second person. The display is designed to work in response to receiving location data from a proximity detector. The display comprises an identifier of the health care worker and real-time location information for the health care worker.

DETAILED DESCRIPTION OF THE PREFERRED EMBODIMENTS

Figure 1A:
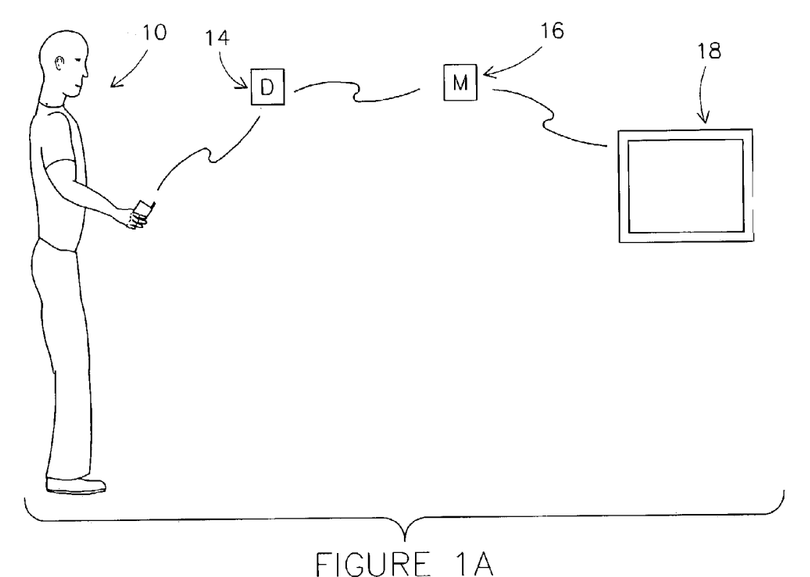
FIGS. 1A–B show a system for detecting the location of a subject of interest according to two embodiments of the invention using wireless proximity detectors.

FIG. 1A shows a system for detecting the location of a subject of interest according to one embodiment of the invention. FIG. 1A shows a subject of interest 10 associated with a wireless identification device 12. Also shown are a wireless proximity detector 14, a monitor 16, and a data output unit 18.

The wireless proximity detector 14 detects a unique signal identifier associated with the identification device 12 that is physically associated with the subject of interest 10. The monitor 16 wirelessly monitors the proximity detector 14 to determine which unique signal identifiers have been identified by the wireless proximity detector 14. The monitor then generates a data signal representative of which signal identifiers have been detected by the proximity detector; the monitor transmitting the data signal wirelessly to the display 18. As a result, the display 18 can then display location information in response to the data signal.

Figure 1B:
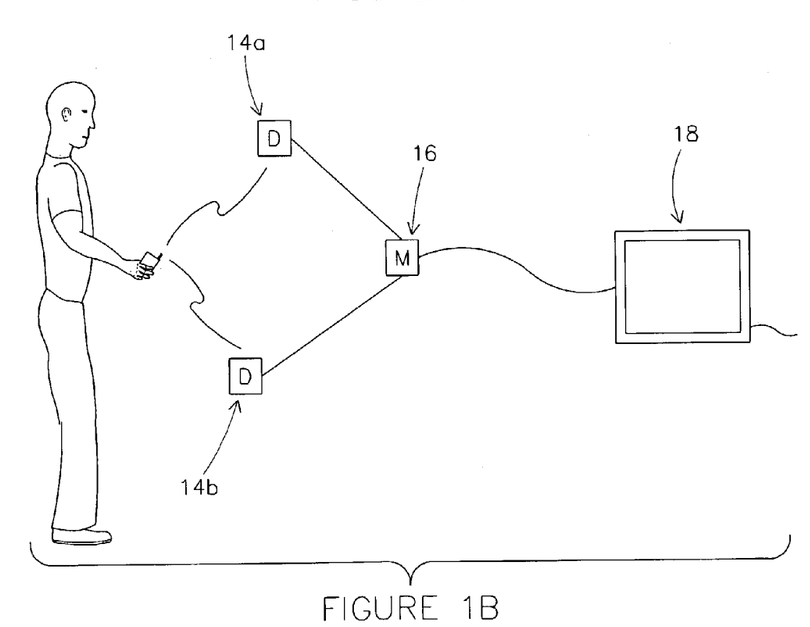

FIG. 1B shows a monitor 16 that is monitoring two proximity detectors 14a and 14b. The monitor 16 is connected to the proximity detectors 14a and 14b via a data connection. The monitor 16 may be integral with one of the proximity detectors 14a and 14b, or it may be a separate unit. The monitor 16 can then generate a data signal and send it to the printer 18b where the data can be outputted as a printed display. The unique signal identifier is being detected by both proximity detectors 14a and 14b in this illustration.

Figure 2:
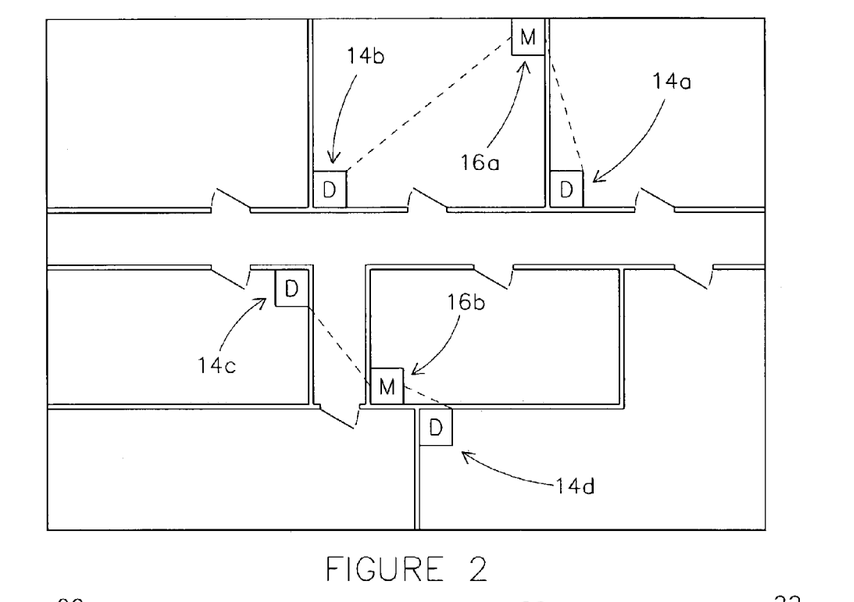
FIG. 2 shows the arrangement of proximity detectors and monitors in one embodiment.

FIG. 2 shows the arrangement of proximity detectors 14a–d and monitors 16a and 16b according to one embodiment of the invention. The proximity detectors are arranged throughout an area of the building. Monitor 16a monitors proximity detectors 14a and 14b while monitor 16b monitors proximity detectors 14c and 14d.

The monitors 16a and 16b may be coupled together to generate information, each may send a data signal to a data output device, or each may send a data signal to a separate unit that processes and/or stores the information. For instance, a monitor 16 may be connected to a data output unit 18 via a network (wired, wireless, etc.) and the system may have a central server 50 that facilitates storage of the location information. A data output unit 18 may output data stored and/or processed in some other part of the system, which location information was based upon the data signals generated by the monitors 16.

The wireless proximity detectors 14*a–d* in this embodiment would likely detect signals generated outside the room in which the detector is located. That is, preferably, the proximity detector can detect a signal in all directions and preferably is not consistently eliminated (although it is likely hindered) by interior walls of a building.

Additionally, more than one wireless proximity detector 14*a–d* could detect a given signal identifier. Based upon which proximity detector or detectors detected the unique signal identifier, a location of the subject associated with the signal identifier could be determined. Also, potentially, the strength of the signal detected and the time it takes for the signal to get to a proximity detector could aid in determining the location of the subject of interest. Also, techniques, such as using the Doppler effect, could be used to determine the direction of movement of the subject.

Figure 3:
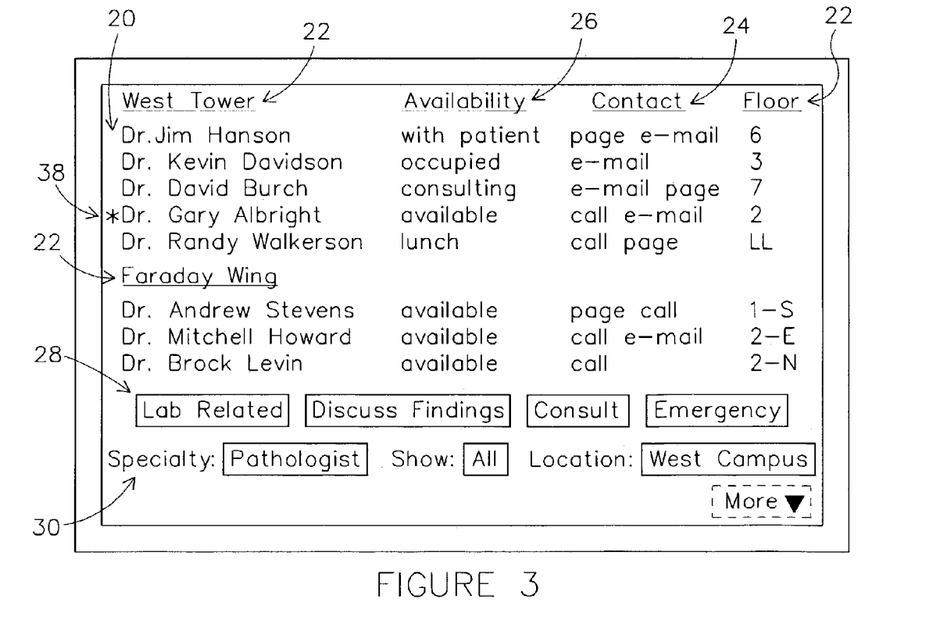
FIG. 3 shows a data output display as a list with a number of options and information.

FIG. 3 shows an output display 20 on a screen that lists the physicians by location according to one embodiment of the present invention. The display 20 includes broad location information 21*a* and 21*b*. The broad location information 21 may be used to better group doctors in a manner that is not too confusing. The display 20 also includes a list of doctor names under the broad location information 21 indicating which doctors, associated with the detected unique signals, are at each location. Additionally, narrow location information 22 is shown, giving the user a better idea of the exact location of the doctor listed.

Also shown is current availability information 26 that lists each doctor's current availability. Availability information could also be by way of calendar information 32. For instance, a link could be created between a doctor and the doctor's schedule. When the link is clicked, the schedule appears. Calendar information 32 is useful for identifying a later time that the doctor is available for a consult or visit. The schedule may also contain features that allow a user to schedule a meeting with the doctor. Availability status may also be displayed as a graphical/visual indicator of the status. For instance, the doctor's name may appear a different color when the doctor is available such as red for unavailable, yellow for 'contact by pager only', and green for available. Also, a doctor's name may fail to appear in the list if the doctor is unavailable or does not want to be contacted. Further, an X may appear over an unavailable doctor, a patient icon may appear next to a doctor who is with a patient, etc. Other visual indications of availability may include an indented name for unavailable, a bold name for availability, etc.

Also shown is contact information 24 that lists ways to contact the doctor. The contact information 24 displayed can be set to display certain types of contact depending on the availability status of the physician. Also, the contact information 24 can be configured to display modes of contact based on availability status that are different for each doctor depending on the doctor's preference or by specialty (some specialties may react less favorably to being called or interrupted). The contact information 24 may additionally be linked to a device that contacts the doctor. For instance, clicking on 'e-mail' might launch an e-mail application which is preaddressed to the doctor, or clicking on the 'call' button might facilitate audio communication between the user and the doctor (over a network, or over a phone system, etc.).

Further, pre-selected messages 28 are shown. These pre-selected messages 28 may be useful if the user is observing the display 20 on a device without easy means of text input, such as a personal digital assistant or cellular phone. Selecting a pre-selected message 28 followed by linking to a contact may allow the user to send the doctor a brief reason for contact. Brief reasons for contact may also be preferable if the doctor is receiving the message on a device with a small screen such as a pager or cellular phone screen. This would allow a doctor to scan the pre-selected message 28 and decide if further contact is desired.

Additionally, sorting options 30 are provided to allow a user to narrow the number of doctors displayed by listing those that most fit the user's needs; they allow the information to be displayed by category. The sorting options 30 that are listed include 'specialty', 'show by availability', and 'location'. Sorting by specialty allows a user to narrow the search based upon the services needed, or the field that the person for whom they are looking is practicing. Showing based on availability is most useful for someone who needs to find an available doctor in the near future. The sorting can be done on current availability, future availability, etc. Showing based on location allows a user to find doctors meeting their criteria in the area. Sorting can also be done by job title, job duties, position, team, patient, alphabetically, name, and any other criteria that may be useful.

Also shown is best subject indicator 39 that indicates the best subject for the user to contact. The program may find the closest doctor, the closest available doctor, etc. This allows a user to better select the doctor that may be able to give the promptest service. Best subject indicator 39 may list more than one doctor and may also list all doctors meeting certain criteria (such as team, location, experience, training, etc.). Best subject indicator 39 may be graphical, visual, audible, or any other indicator and need not appear along with the doctor's name (for instance the best subject may appear in a special box removed from the other names).

While FIG. 3 has been described with respect to doctors, the embodiment could apply to any subject of interest 10. For instance, in a health care setting nurses, physical therapists, wheel chair pushers, social workers, health insurance and financial staff, and many other people with various positions may be desirable to track and/or quickly contact.

Figure 4:
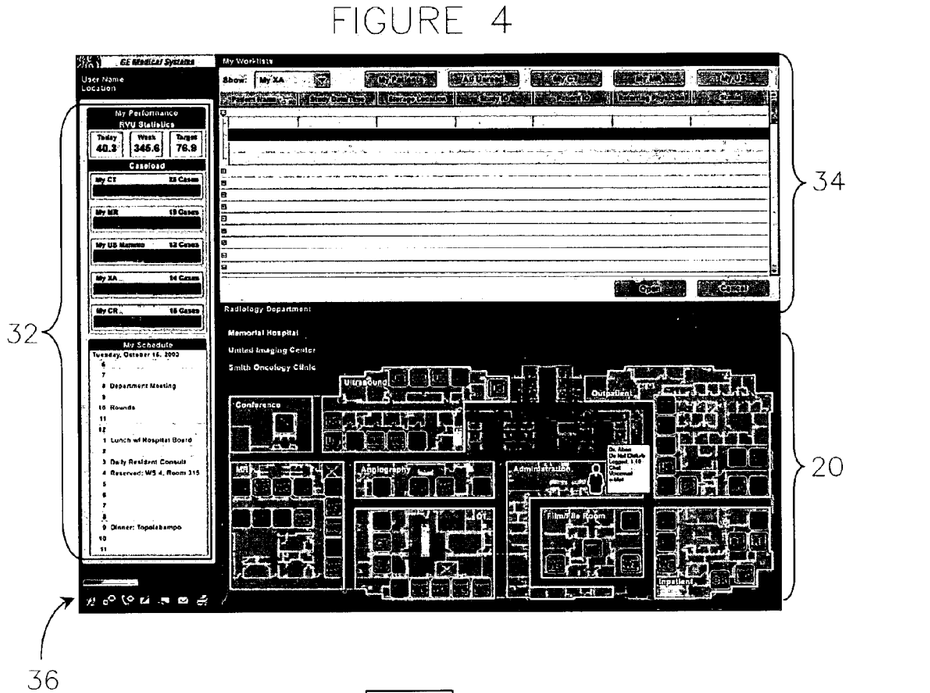
FIG. 4 shows a data output display as a map where the subject of interest is represented as an icon on the map.

FIG. 4 shows another embodiment of the data output display 20 according to another embodiment of the invention. The display 20 is a graphical display, and more specifically, it is a map of a hospital. The subject of interest 10 is represented by an icon on the map, placed in a location where the subject of interest 10 is detected to be located.

The display 20 includes broad location information 21 when the user selects a floor or area of a map to be displayed. Such selection may be done by using sorting options 30 that are expandable. The display 20 also includes narrow location information 22 as department areas within the map being displayed.

The sorting options 30 can also be configured to allow a user to connect to more than one discrete location which has monitoring. For instance, a private practice internist that needs to contact an endocrinologist can first view the hospital at which they admit patients, but if no endocrinologist is available at the admitting hospital, the internist can the log into other hospital location systems to determine if the other hospital has endocrinologists that are available and are in a location that the internist can contact. Also, identifying a staff member in a file room allows a private practice doctor using a hospital's resources to contact the correct person who can send the doctor results obtained using the hospital's resources.

Sorting options 30 configured in this way can also be used to identify discrete units within a hospital campus, especially where hospital campuses are fairly large and have multiple departments. A hospital may set up individual discrete units as a way of slowly integrating a locating system, area by area, into the hospital without making large up-front expenditures. For instance, a hospital might initially set up a location detection system in an area such as an emergency room department where knowing what staff is available, and how far away staff is located, may be very valuable tools. The hospital may later decide to expand coverage, but the technology might have changed. A hospital might then keep the old ER monitoring system distinct from the new technology system being added. Having a display 20 that can operate with both of the systems would be advantageous because it would save the hospital money, and would take away some of the disincentive for a hospital to expand its coverage. A large hospital may also use separate systems if tracking throughout the entire campus would be too difficult or cumbersome for a single system. The hospital may then set up discrete systems for each of the distinct areas. Having a display 20 that could conveniently enable movement between the discrete systems may increase response and usability of a tracking system.

Also shown are action items 36 that allow a user to initiate certain actions without having to search for the items. Some examples of common action items 36 include chat, call, notes, e-mail, print, page, and many other items which enable some action to occur.

Further, calendar information 32 is shown. The calendar information 32 is initially the user's schedule, but clicking on a link can enable display of a subject of interest's 10 schedule. The subject of interest's 10 schedule can replace the user's schedule, can appear side by side with the user's schedule, can overlay the user's schedule in a different font or color, can appear somewhere else on the screen, can appear in a separate window, or any other location. The subject of interest's 10 schedule may show full details, partial details, or only availability. The subject of interest and/or user may customize what schedule information is shown.

Further, more information about the subject of interest can be displayed along with the location. For instance the subject's availability information 26, contact information 24, time information 38, or any other information that may be useful or necessary may be displayed. The further information may appear automatically, may appear only if the subject meets certain criteria (such as availability), may appear only if the user scrolls over or taps on the icon representing the subject, or in response to any other form of enabling the display.

Figure 5A:
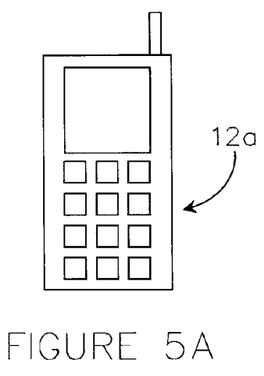
FIGS. 5A–C show some of the devices that can be used as an identification device.
Figure 5B:
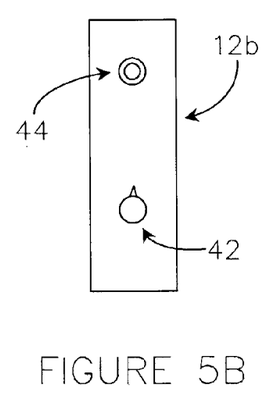
Figure 5C:
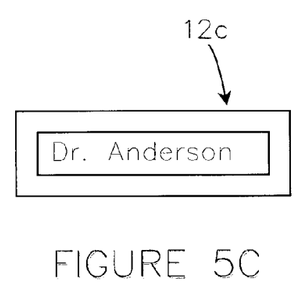
Figure 6A:
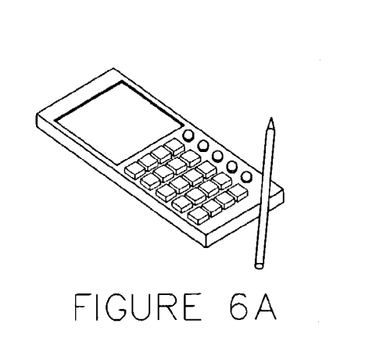
FIGS. 6A–E show some of the devices that can serve as a data output display.
Figure 6B:
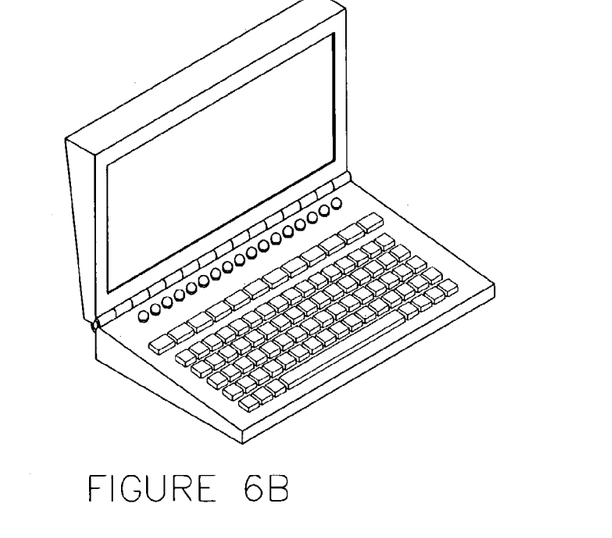
Figure 6C:
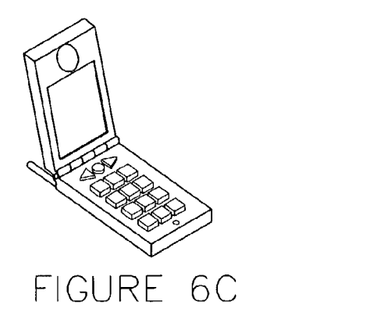
Figure 6D:
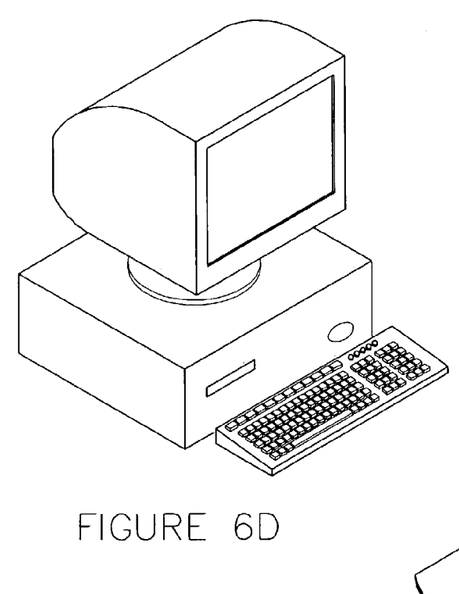
Figure 6E:
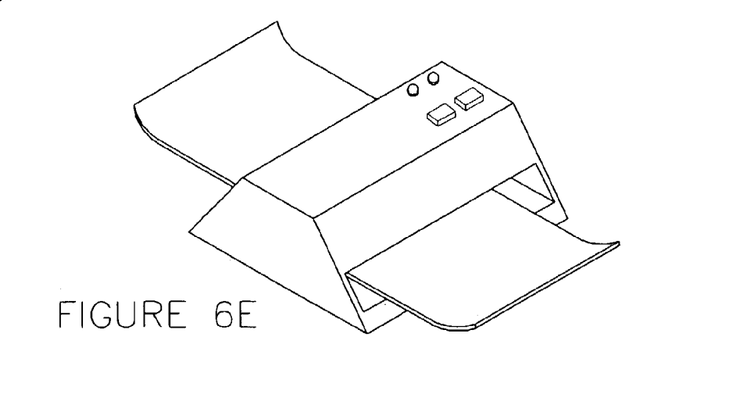

FIGS. 5A–C show some examples of identification devices 12 according to one embodiment of the present invention. The identification device 12 can be any number of devices that have a unique identification signal associated with the device that can be detected by a wireless proximity detector. As seen in FIG. 5a, the identification device can be a cellular phone. A cellular phone 12a can be programmed to have many other options associated with it. For instance, the cellular phone 12a can be linked to a data output unit 18 to allow a user of the data output unit 18 to directly contact the subject 10. Also, text messages can be received by the cellular phone 12a. Additionally, a subject 10 may have the option of sending signals representative of various information from the cellular phone 12a, including an availability signal (a signal representative of the subject's availability). Also, other types of non-location signals (signals indicating information other than location) can be generated by the cellular phone, including task information (information listing the task being undertaken by the subject 10). A location signal and a non-location signal can be one integrated signal that serves two purposes (one location and the other non-location), the signals may be discrete signals, or the signals may be in any other combination.

As seen in FIG. 5B, the identification device 12 can be a simple device 12b whose only feature is having a unique signal. The simple device 12b may be made slightly more useful by adding some additional features. One such feature shown is a switch 42 that can be flipped between various availability settings. In response to the position of the switch 42, various availability signals can be sent. Another potential feature shown is a headphone/microphone jack 44 where the subject can plug in head phones, a microphone, or a combination that allows the doctor to receive messages, send messages, dictate information, communicate with someone (such as a user at a display), etc.

As seen in FIG. 5C, the identification device 12 can be a pager 12c. The pager 12c shown includes an input device 46 that allows a user to select various availability settings, which settings show up on the pager's 12c screen. The pager 12c can also receive text messages and be used as a prompt that someone desires to contact the subject 10.

Other typical devices to be used as identification devices 12 include personal digital assistants and portable personal computers (such as tablet PCs, pocket PCs, and notebook PCs). Also, communication devices such as head phone-microphone combinations that have a unique identification signal would make good identification devices 12. An identification feature could be attached to a clothes pin, a button, a bobby pin, a tag, an adhesive strip, a clasp, or any other fastening device to make the fastening device useful as an identification device 12.

These specific examples are only a small number of examples of devices that could serve as identification devices. An identification device 12 could also include any other subject 10 portable device or subject 10 transport device that is capable of having a unique signal associated therewith, where the signal can be identified by a wireless proximity detector 14.

FIG. 6 shows some devices which may serve as displays 18 according to one embodiment of the present invention. The types of devices that could serve as a display 18 are quite numerous. Some of the preferred devices include portable display devices such as a personal digital assistant (see FIG. 6A), a Tablet PC (see FIG. 6B), and a phone with a screen (see FIG. 6C), and also non-portable display devices such as a computer (see FIG. 6D) or a printer (see FIG. 6E). The smaller and less processing power and memory a display device has, the smaller and less complicated the program should be. Also, such devices may rely more heavily on a central server to run a control program. On the other hand, computing devices with larger amounts of memory and processing power may, but need not, run more of the control program from the device itself. Also, such devices may display more information, have more options, and run more advanced operations. As technology advances, devices capable of running large complicated programs will no doubt get smaller and more portable.

Figure 7:
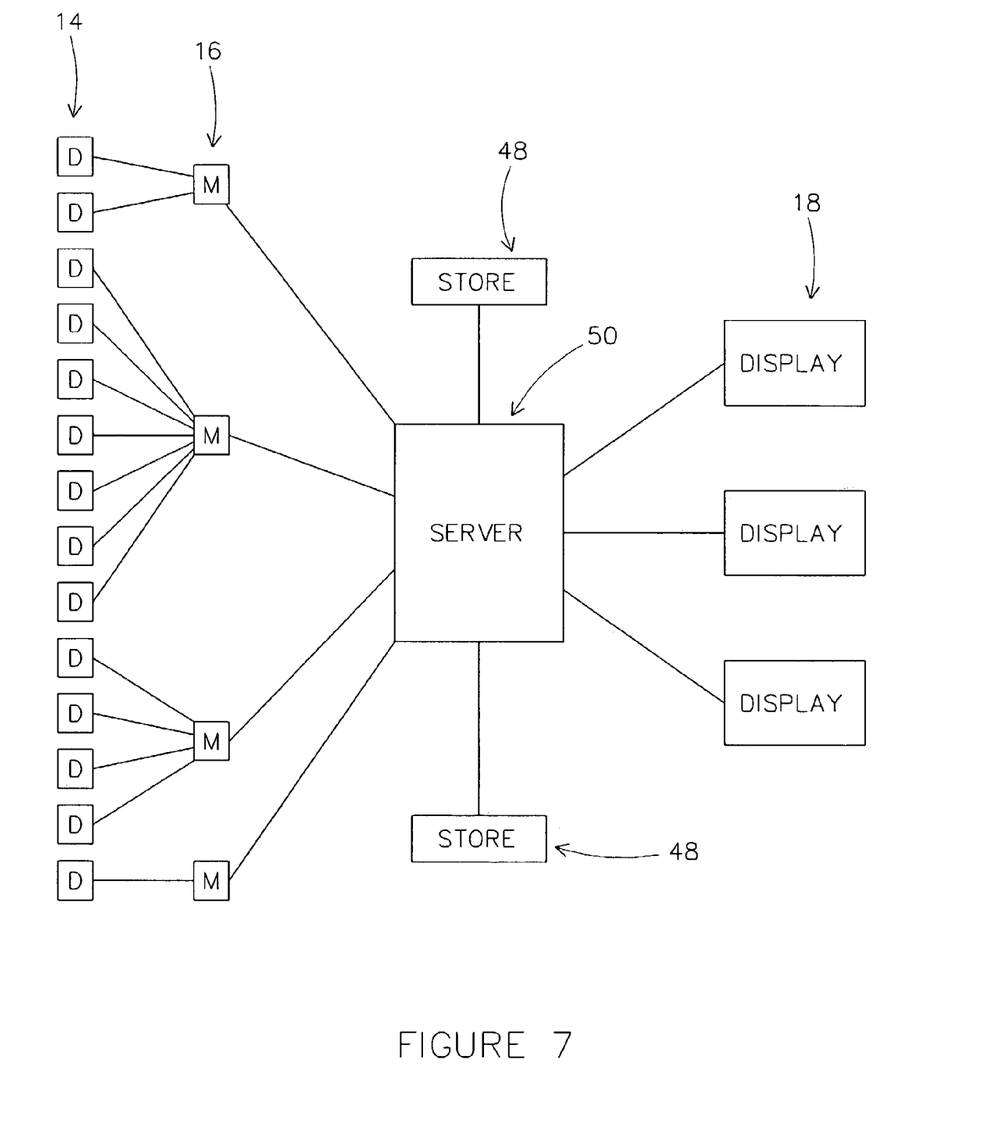
FIG. 7 shows the set-up of a system for wireless monitoring according to one embodiment of the invention.

FIG. 7 is a system layout according to one embodiment of the invention. The system includes wireless proximity detectors 14, monitors 16, data output units 18, data storage devices 48, and a server 50. The wireless proximity detectors 14 detect unique identification signals. The monitoring units 16 monitor the wireless proximity detectors 14; monitoring which signal identifiers have been detected by the wireless proximity detectors 14 they monitor. The monitoring units 16 generate a data signal representative of which signal identifiers have been detected by the wireless proximity detectors 14. The information then goes to a server 50, as shown a central server that receives signals from all of the monitors. The monitors 16 themselves can, although preferably do not, serve the same function as the server 50. The server 50 can then supply information to various data output units 18, such as displays or printers. Some systems will likely not continuously update information for reasons of processing power and size of the network being monitored. Such systems will likely include data storage units 48 that can store information that has been sent to the central processor. Such systems still provide real-time location information of the subject of interest 10; monitoring every so many minutes still provides location information based on where the subject actually is detected, not based on where the subject states they are located, where a subject should be based on their schedule, etc.

It is also preferable that the system continuously tracks the subject, not just tracking the subject in certain situations, such as emergency situations. If a subject is not continuously tracked, information provided to a user will likely not be as useful for planning or other activities.

Additionally, the system preferably broadly tracks the location of the subject, i.e. the system preferably tracks the exact location of the subject, not just when they pass certain check points. Although not preferred, the system could operate by determining when the subject passes by set points, or could include a combination of set points and broad tracking.

The data storage units 48 may also receive information directly from the monitors 16 or may provide information directly to the data output units 18. If the data storage units 48 serve both functions, then they are essentially acting as servers 50—in which case the server 50 and the data storage unit 48 are a single unit that can be considered both a data storage unit 48 and a server 50. This two function, one unit considered to be two units for the sake of interpreting the claims can be applied to any combination of the devices.

Figure 8:
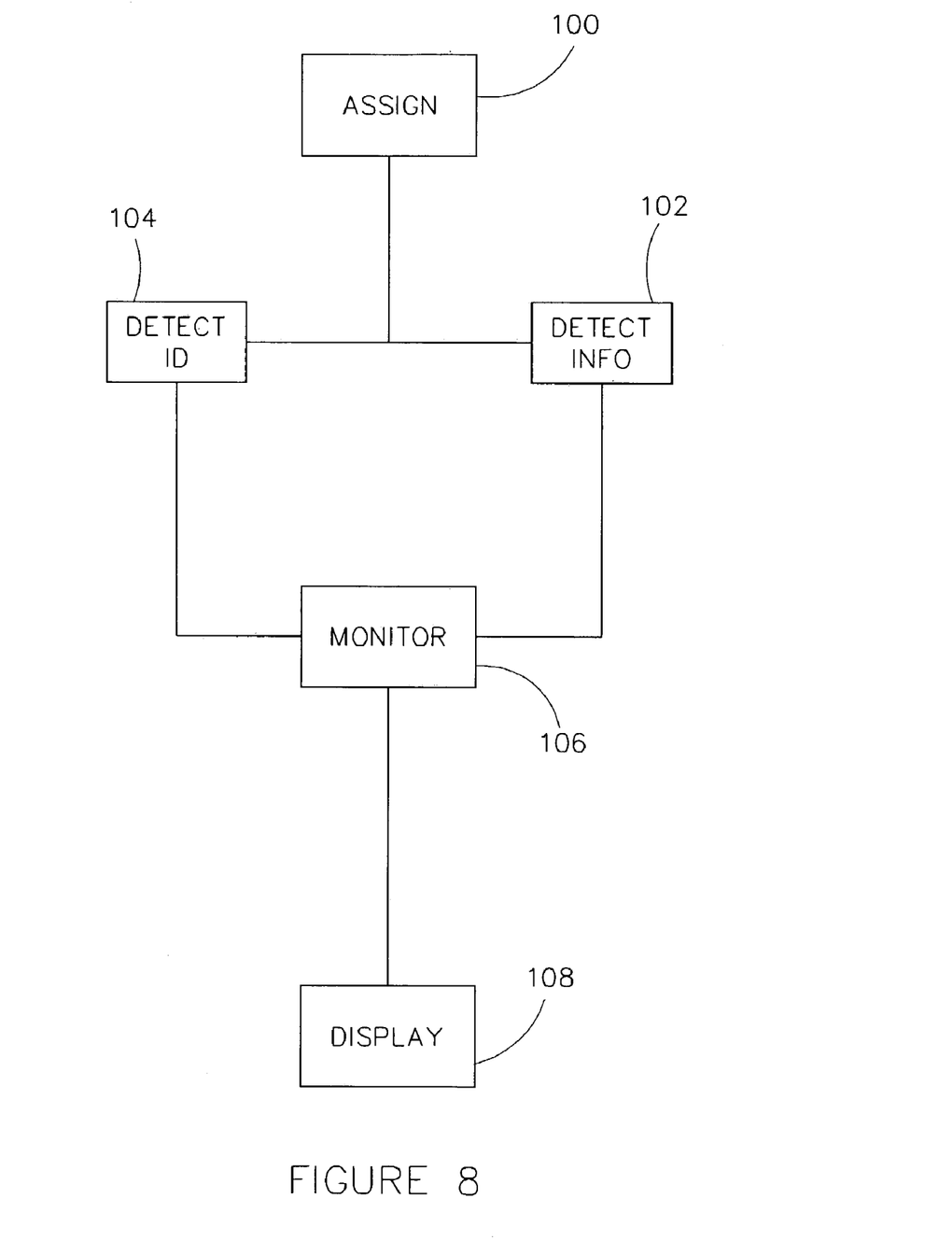
FIG. 8 is a flow chart according to one embodiment of the invention.

FIG. 8 is a method that can be used according to one embodiment of the invention. The method can include assigning a unique signal identifier to a subject of interest at step 100. This allows a subject 10 to be identified based upon a signal that is detected. This may be accomplished by obtaining a scanned signal at a point where a device can recognize the subject to be assigned. This can also be accomplished by using a code translator to translate certain signals to prompt certain displays—such as "10110010" means display "Bob Smith". This step could also be carried out in a number of other ways, including sending the assigning information as part of a signal being detected. The method also includes detecting the signal identifier using a wireless proximity detector at step 104 and detecting a non-location information signal at step 102. The method further includes monitoring the wireless proximity detector for detection of the unique signal identifier at step 106. The method also involves displaying output data representative of the location of the subject of interest 10 at step 108. The display at step 108 can be carried out by displaying the subject of interest 10 as an icon on a map. The method can also include displaying non-location data related to the output data along with the output data such as information data—data providing information about the subject of interest other than location. The information data can include contact data, calendar data, availability data, or some other type of informational data. The information data can be displayed as a graphic representative of the data as mentioned earlier for non-location information generally (i.e. color, symbol, etc.). This method is particularly useful in a health care setting to monitor health care workers such as hospital psychologists, doctors, nurses, technicians, and administrators.

Tracking a person can be done by tracking a signal assigned to them directly, or it can be done by tracking a signal assigned to them indirectly. An example of signal that has been assigned indirectly is a wheel chair gets assigned a signal, and the person gets assigned to the wheel chair. The signal on the wheel chair being pushed with the person can be used to track the person; essentially, tracking the wheel chair is the same as tracking the person when the person is assigned to the wheel chair. Thus, the signal has been indirectly assigned to the person.

While the signal of the identification device 12 can use any wireless technology, it preferably uses a radio frequency (RF) signal for identification, such as a passive RF identification signal. More preferably, it uses Bluetooth™ technology, the Bluetooth trademark owned by Bluetooth SIG, Inc. Bluetooth wireless technology provides wireless connections; enabling links between mobile computers, mobile phones, portable handheld devices, and connectivity to the Internet. Bluetooth tends to have a low power consumption and a low cost.

The Bluetooth wireless specification includes both link layer and application layer definitions for product developers which supports data, voice and content-centric applications. Radios that comply with the Bluetooth™ wireless specification operate in the unlicensed, 2.4 GHz ISM (Industrial, Scientific and Medical) Band radio spectrum. These radios use a spread spectrum, frequency hopping, full-duplex signal at up to 1600 hops/sec. The signal hops among 79 frequencies at 1 MHz intervals to give a high degree of interference immunity. Bluetooth's synchronous bands are geared to carry relatively high-quality voice, while the asynchronous communication will support data at slightly more than 700 Kbps.

Distance for standard devices is limited to about 10 meters, but can be expanded to much larger distances (such as 100 meters) if desired. Once the devices are within the distance boundary, the devices can be connected automatically. It also provides a fast and secure transmission of voice and data even when the devices are not within line of sight.

Advanced error-correction methods, encryption and authentication routines are used to protect data for a user's privacy. Further, the technology provides a high transmission rate. The Bluetooth wireless technology supports both point-to-point and point-to-multipoint connections. Even though Bluetooth wireless protocol is currently preferred, other wireless systems and technologies may also be used.

A unique signal could be a unique wavelength, use a unique standard, or use some other method of wireless identification using a signal, but preferably means having a unique code coupled to a wireless signal. The unique identifier could be a consistent identifier for each device or could be changeable, such that when a different user has a device, the unique signal could be changed.

The invention has been described with reference to various specific and illustrative embodiments and techniques. However, it should be understood that many variations and modifications may be made while remaining within the spirit and scope of the invention. For instance, much of the discussion related to tracking doctors, but it should be understood that any person or object could be tracked in a health care facility. For instance, location information relating to patients may be helpful for reception staff, especially if a patient is not in their assigned room at the time. Also, a nurse may want to know where the food delivery people are, and when they will be delivering food to their patients. Additionally, a physician may want to contact a technician to talk about a test that was run, or will be run. Further, many health care facilities have transportation staff that transport patients from one location to another. Knowing the location of the transportation staff would likely be very helpful for tracking patients and for the purpose of planning.

The various health care facility workers to be tracked can be placed into five main categories: health care providers, who actually provide treatment and diagnostic services (such as nurses, doctors, technicians, etc.); auxiliary well being care providers, who provide care not related to treatment (such as social workers); administration staff, who provide administrative services such as financial, regulatory, and decision-making services; security staff, who provide security services and ensure the safety of the health care facility; and support staff, who provide all other services such as transporting patients, receptionists, and kitchen staff.

The system is most useful in a health care facility for tracking well being providers, especially doctors and nurses. Other staff who it may be important to track are auxiliary well being care providers, some administration staff who are necessary to authorize care, and, in some circumstances, support staff when knowing the location of the support staff facilitates planning (such as food delivery and wheel chair transport staff).

What is claimed is:

1. A system for tracking one or more caregivers in a health care facility, each caregiver having at least one identification device with a unique signal identifier, the system comprising:
   a wireless proximity detector capable of detecting a signal identifier positioned in the health care facility;
   a monitoring unit that monitors the proximity detector by monitoring which signal identifier has been detected by the proximity detector, the monitoring unit generating a data signal representative of which signal identifier has been detected by the proximity detector; and
   a data output unit separately coupled to and receiving the data signal from the monitoring unit, the data output unit configured to generate and display real-time location data based upon the data signal;
   wherein the proximity detector further detects a real-time non-location signal from a signal device;
   wherein non-location data is displayed along with the location data; and
   wherein the non-location data is selected from a group consisting of calendar information and availability information.

2. The system of claim 1, wherein the wireless proximity detector uses a radio frequency and is capable of detecting more than one identification device at a time.

3. The system of claim 1, comprising at least one additional wireless proximity detector positioned in the health care facility, wherein the monitoring unit monitors each of the plurality of proximity detectors and monitors which signal identifier has been received by each proximity detector.

4. The system of claim 1, wherein the non-location signal is an availability signal.

5. The system of claim 1, wherein the non-location data is displayed in the form of a color representative of the non-location data.

6. The system of claim 1, further comprising controls, coupled to the display, which allows the caregiver to be contacted.

7. The system of claim 1, wherein the data output unit is a display configured as one of a group consisting of a map, a list, or a chart.

8. The system of claim 7, wherein the signal identifier is a radio frequency signal and the proximity detector is capable of detecting the radio frequency signal.

9. The system of claim 1, wherein the data generated by the data output unit can be displayed by category.

10. The system of claim 9, wherein the category is selected from a group consisting of a medical specialty, a job classification, and an availability status.

11. The system of claim 1, wherein the display displays a closest caregiver of interest meeting selected criteria.

12. The system of claim 1, further comprising a plurality of signal devices, each with a unique signal identifier.

13. The system of claim 12, wherein at least one signal device can generate an availability signal.

14. The system of claim 12, wherein at least one signal device further comprises a contact unit.

15. The system of claim 1, wherein the caregiver is a doctor and the location is a hospital and the data output unit generates location data representing the location of the doctor in the hospital.

16. A method for tracking a caregiver in a health care facility, comprising:
   assigning a unique signal identifier to the caregiver;
   detecting the signal identifier using a wireless proximity detector positioned in the health care facility;
   monitoring the proximity detector for detection of the unique signal identifier and generating a signal representative of the detected identifier;
   receiving the generated signal and displaying output data representative of the real-time location of the caregiver in the health care facility, based on the monitoring wherein the displaying is effectuated in a separate location from the monitoring;
   displaying real-time information data related to the output data along with the output data; and
   wherein the information data is selected from a group consisting of calendar data and availability data.

17. The method of claim 16, wherein the output data is displayed as an icon on a display map.

18. The method of claim 16, further comprising continuously tracking the person.

19. A display for indicating a location of a health care facility staff person to a second person in response to receiving location data from a proximity detector positioned with the health care facility which detects a person's identifier, the display comprising:
   a monitoring unit separately coupled to the display, the monitoring unit configured to monitor the proximity detector and transmit a signal representative of the detected identifier to the display;
   an identifier of the health care facility staff person; and real-time location information representing the position of the health care facility staff person in the health care facility;

wherein real-time subject information of the health care facility staff person is displayed along with the location of the health care facility staff person, the subject information selected from a group consisting of availability information, and calendar information.

20. The display of claim 19, wherein the location is displayed in a manner selected from a group consisting of a list, a chart, and a graphical representation.

21. The display of claim 20, wherein the display is a graphical representation and the graphical representation is a map, and the health care facility staff person is displayed as an icon on the map.

22. The display of claim 19, wherein the subject information is represented graphically.

23. The display of claim 19, wherein the subject information is schedule information and the schedule information is displayed as a result of a user selecting to display schedule information.

24. The display of claim 19, wherein the real-time location information is displayable by category.

25. The display of claim 19, further comprising a communication tool.

26. The display of claim 19, wherein the display represents a location of a health care facility staff person selected from a group consisting of a health care provider, auxiliary well being care provider, and a support staff person.

27. The display of claim 26, wherein the display represents a location of a health care provider.

* * * * *